United States Patent [19]

Kuhn

[11] Patent Number: 4,659,857

[45] Date of Patent: Apr. 21, 1987

[54] INSECTICIDAL CINNAMAMIDE COMPOUNDS AND METHOD FOR CONTROLLING INSECTS THEREWITH

[75] Inventor: David G. Kuhn, Bucks County, Pa.

[73] Assignee: American Cyanamid Company, Stamford, Conn.

[21] Appl. No.: 772,511

[22] Filed: Sep. 4, 1985

[51] Int. Cl.$^4$ .................. C07C 143/68; C07C 103/82
[52] U.S. Cl. ...................................... 558/58; 558/415; 564/153; 564/154; 564/155; 564/157; 564/158
[58] Field of Search ............... 564/158, 157, 155, 154, 564/153; 558/58, 415

[56] References Cited

PUBLICATIONS

Richter et al., C. A., 80, 70495r, (1974).

*Primary Examiner*—Nicky Chan
*Attorney, Agent, or Firm*—Estelle J. Tsevdos

[57] ABSTRACT

The present invention relates to novel cinnamamide compounds and a process for the preparation thereof. The compounds of the invention are useful for controlling insects and acarina.

13 Claims, No Drawings

INSECTICIDAL CINNAMAMIDE COMPOUNDS AND METHOD FOR CONTROLLING INSECTS THEREWITH

BACKGROUND OF THE INVENTION

The present invention relates to novel cinnamamide compounds and also to methods for controlling insects and acarina with cinnamamides.

Although there is a brief report of the preparation of α-benzamido-p-cyano-N-isopropylcinnamamide in the literature (Chemical Abstracts Volumn 80: 70495 (1974)), there is no mention of the use of said compound as an insecticidal or acaricidal agent. The compounds of the invention have been found to be effective such agents especially as contact and stomach poisons of insects and/or acarina. Furthermore, these agents are systemically effective when applied to the root systems of growing, living plants or to the soil or water in which said plants are grown. When so applied, the plant is protected through an extended period of active growth.

It is an object of the present invention, therefore, to provide the novel cinnamamides as insecticidal and acaricidal agents.

It is a further object of the invention to provide a method for controlling insects and acarina by using the compounds of this invention. Specifically, it is an object of the invention to provide these compounds as stomach and contact poisons.

Additionally, the compounds of the present invention are advantageous in systemically protecting growing, living plants from insects and acarina which infest such plants through an extended period of active growth.

Furthermore, methods for preparing the compounds of the invention are disclosed.

These and further objects will become more apparent by the more detailed description of the invention herein provided.

SUMMARY OF THE INVENTION

The novel compounds of the present invention are represented by formula (I):

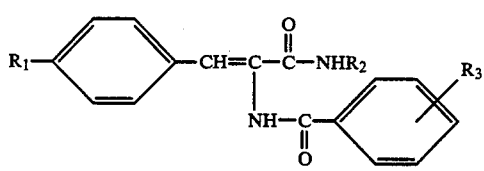

wherein $R_1$ is hydrogen, $C_1$-$C_4$ alkyl, $C_1$-$C_4$ alkoxy, $CF_3CH_2O$, $CF_3O$, F, Cl, Br, $CF_3$, $NO_2$, $CF_2HS$, $CF_2HO$, $(R)_2N$, $R$-$SO_3$, $R$-$CO$-$NH$ or $CHY_2CF_2O$; Y is F, Cl or Br; R is $C_1$-$C_4$ alkyl; $R_2$ is $CH_3$, $C_2H_5$, branched $C_3$-$C_5$ alkyl or cyclopropyl; $R_3$ is hydrogen, Cl, $C_1$-$C_4$ alkyl, $C_1$-$C_4$ alkoxy or CN.

Preferred compounds of these new cinnamamides include structures wherein $R_1$ is $CF_3CH_2O$, $CF_3O$, F, Cl, Br, $CF_3$, $NO_2$, $CF_2HS$, $CF_2HO$, $R$-$SO_3$, $R$-$CO$-$NH$ or $CHY_2CF_2O$; $R_3$ is hydrogen and Y, R and $R_2$ are as above described.

Illustrative of some of the most preferred compounds of the present invention are α-benzamide-N-isopropyl-p-(1,1,2,2-tetrafluoroethoxy)cinnamamide, α-benzamido-p-chloro-N-isopropylcinnamamide, α-benzamido-p-fluoro-N-isopropylcinnamamide, α-benzamido-p-hydroxy-N-isopropylcinnamamide methanesulfonate (ester), α-benzamido-N-cyclopropyl-p-(trifluoromethoxy)cinnamamide, α-benzamido-N-isopropyl-p-(trifluoromethoxy)cinnamamide, α-benzamido-p-(difluoromethoxy)-N-isopropylcinnamamide, α-benzamido-N-cyclopropyl-p-fluorocinnamamide, α-benzamido-N-cyclopropylcinnamamide, α-benzamido-N-sec-butyl-p-(difluoromethoxy)cinnamamide and α-benzamido-p-hydroxy-N-isopropylcinnamamide ethanesulfonate (ester.)

DETAILED DESCRIPTION OF THE INVENTION

Method of Preparation

The novel cinnamamide compounds of the present invention, illustrated by formula (I) above, can be prepared by reaction of an oxazolinone of formula (II):

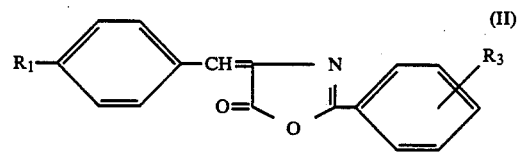

wherein $R_1$ is hydrogen, $C_1$-$C_4$ alkyl, $C_1$-$C_4$ alkoxy, $CF_3CH_2O$, $CF_3O$, F, Cl, Br, $CF_3$, $NO_2$, $CF_2HS$, $CF_2HO$, $(R)_2N$, $R$-$SO_3$, $R$-$CO$-$NH$ or $CHY_2CF_2O$; Y is F, Cl or Br; R is $C_1$-$C_4$ alkyl and $R_3$ os H, Cl, $C_1$-$C_4$ alkyl, $C_1$-$C_4$ alkoxy or CN; with an excess of a formula (III) alkyl amine:

wherein $R_2$ is $CH_3$, $C_2H_5$, branched $C_3$-$C_5$ alkyl or cyclopropyl.

This reaction preferably is conducted in the presence of an aprotic solvent such as benzene, toluene, xylene or the like. The alkyl amine (III) generally is admixed with the oxazolinone (II) at ambient temperature with an exotherm usually developing. The reaction mixture is stirred until the exotherm ceases. Thereafter, stirring is continued until the mixture cools to about 20° C. to 25° C. The cooled reaction mixture is then heated to refluxing temperature for an extended period of time, usually from about one to three hours. Thereafter, the reaction mixture is cooled and filtered to recover the formula (I) cinnamamide.

Preparation of the formula (II) oxazolinones is readily achieved by reacting approximately equimolar amounts of a benzoyl halide, such as represented by formula (IV):

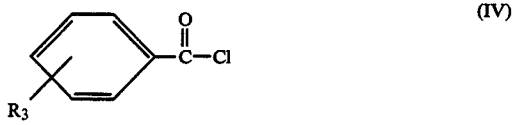

wherein $R_3$ is hydrogen, Cl, $C_1$-$C_4$ alkyl, $C_1$-$C_4$ alkoxy or CN; with glycine in the presence of aqueous base. The reaction mixture is then acidified with a strong mineral acid such as hydrochloric acid to yield the appropriately substituted hippuric acid depicted by formula (V):

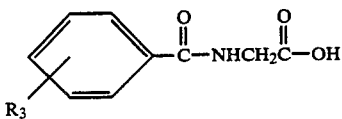

wherein $R_3$ is as described above.

Reaction of the formula (V) hippuric acid with approximately equimolar amounts of an appropriately substituted benzaldehyde represented by formula (VI):

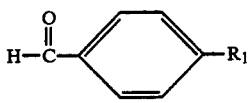

wherein $R_1$ is hydrogen, $C_1$-$C_4$ alkyl, $C_1$-$C_4$ alkoxy, $CF_3CH_2O$, $CF_3O$, F, Cl, Br, $CF_3$, $NO_2$, $CF_2HS$, $CF_2HO$, $(R)_2N$, $R-SO_3$, $R-CO-NH$ or $CHY_2CF_2O$; wherein Y is F, Cl, or Br and R is $C_1$-$C_4$ alkyl; and anhydrous sodium acetate in the presence of acetic anhydride yields the desired oxazolinone of formula (II). As indicated above, the oxazolinones are then converted to the insecticidally and acaricidally effective formula (I) cinnamamides of the present invention.

The above reactions are illustrated in Flow Diagram I.

FLOW DIAGRAM I

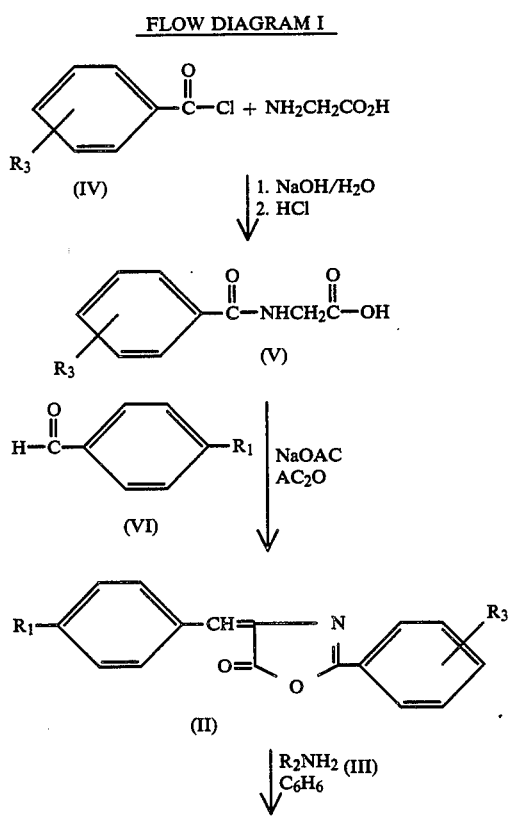

-continued
FLOW DIAGRAM I

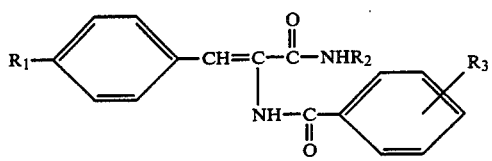

METHOD OF USE

The cinnamamide compounds of the present invention are particularly effective for protecting crops, such as rice, grown in flooded paddies and irrigated crop plants, where the active compounds are dispersed in the water of the flooded paddies or applied to the soil in the locus of the irrigated plots. About 10 ppm to 10,000 ppm, preferably 100 ppm to 5,000 ppm, of the active cinnamamide dispersed in the water is effective for protecting crops from attack by insects and acarina.

When the active compounds are applied to the soil, about 0.25 kg/ha to 8 kg/ha of active ingredient is sufficient to protect the crops against attack by insects and acarina.

It also has been found that the compounds of the present invention are especially effective for controlling Lepidopterous, Dipterous, Homopterous, Coleopterous, Hemipterous insects, as well as acarina, particularly plant mites. For instance, the compounds of the present invention are effective against such pests as *Heliothis virescens* (tobacco budworm), *Spodoptera eridonia* (third-instar larvae, southern armyworm), *Aropheles quadrimaculatus* (adult common malarial mosquito), *Lygris lineolaris* (adult tarnished plant bug) and *Blattella germanica* (adult male German cockroach), as well as others.

Furthermore, the compounds of the invention also are useful as systemically effective agents against *Tetranychus urticae* (P-resistant strain), *Spodoptera eridonia* (adult two-spotted spider mite), *Spodoptera eridonia* (third-instar larvae, southern armyworm) and *Empoasca abrupta* (adult western potato leafhopper), as well as others.

Although the cinnamamides of the present invention are effective for controlling insects and acarina when employed alone, they may be used in combination with other biological chemicals, including other insecticides, acaricides and fungicides. For example, the cinnamamides of this invention may be used effectively in conjunction or combination with phosphates, carbamates, pyrethroides, formamidines, chlorinated hydrocarbons, halobenzoylureas and the like.

Among the pesticides contemplated for use in combination treatments with the cinnamamides of this invention are:

diethyl(dimethoxyphosphinothioylthio)succinate;
O,O-dimethyl O-[3-methyl-4-(methylthio)-phenyl]-phosphorothioate;
(RS)-a-cyano(3-phenoxyphenyl)methyl (RS)-4-chloro-a-(1-methylethyl)benzeneacetate;
(RS)-a-cyano(3-phenoxyphenyl)methyl (1RS)-cis,trans-3-(2,2-dichloroethenyl)-2,2-dimethyl cyclopropanecarboxylate;

(±)-a-cyano(3-phenoxyphenyl)methyl (+)-4-difluoromethoxy-a-(1-methylethyl)benzeneacetate;
(3-phenoxyphenyl)methyl (1RS)-cis,trans-3-(2,2-dichloroethenyl)-2,2-dimethylcyclo-propane-carboxylate;
2,2-bis(p-methoxyphenyl-1,1,1-tri-chloroethane;
4,4'-dichloro-a-trichloromethylbenzyhydrol;
3-(dimethoxyphosphinyloxy)-N,N-dimethyl-cis-crotonamide;
dimethyl 2,2-dichlorovinyl phosphate;
dimethyl-1,2-dibromo-2,2-dichloroethyl phosphate;
2,4-dinitro-6-(2-octyl)phenyl crotonate;
dimethyl 2-chloro-2-diethylcarbamoyl-1-methyl vinyl phosphate;
N-methyl-1-naphthyl carbamate;
O,O-diethyl-S-(ethylthiomethyl)phosphorodithioate;
O,O-dimethyl-S-(ethylthiomethyl)phosphorodithioate;
O,O-dimethyl S-(4-oxobenzotriazine-3-methyl)-phosphorodithioate;
2,3-p-dioxane S,S-bis(O,O-diethylphosphorodithioate);
O,O-diethyl O-(2-isopropyl-4-methyl-6-pyrimidinyl)-phosphorothioate;
O,O-dimethyl S-(N-methylcarbamoylmethyl)phosphorodithioate;
O,O-diethyl O-p-nitrophenyl phosphorothioate;
O,O-dimethyl O-p-nitrophenyl phosphorothioate;
O,O-dimethyl O-(3-methyl-4-nitrophenyl)thionophosphate;
O,O-dimethyl S-p-chlorophenylthiomethyl phosphorodithioate;
methyl-4-dimethylamino-3,5-xylyl carbamate;
2,2-bis(p-chlorophenyl)-1,1,1-trichloroethane;
dichlorodiphenyl dichloroethane;
chlorinated camphene;
terpene polychlorinate;
O,O,O',O'-tetramethyl-O,O'-thiodi-p-phenylene phosphorothioate;
O,O,O',O'-tetraethyl S,S'-methylene bis-phosphorodithioate;
dimethyl 2-methoxycarbonyl-1-methylvinyl phosphate;
O,O-diethyl S-p-chlorophenylthiomethyl phosphorodithioate;
6,7,8,9,10,10-hexachloro-1,5,5a,6,9,9a-hexahydro-6,9-methano-2,4,3-benzodioxathiepin-3-oxide;
2,4,5,4'-tetrachlorodiphenyl sulphone;
alpha-methylbenzyl 3-(dimethoxyphosphinyloxy)cis-chrotomate;
2-(2-butoxyethoxy) ethyl ester;
bis(dialkylphosphinothionyl)disulfide;
O,O-dimethyl O-2-chloro-4-nitrophenyl phosphorodithioate;
(S)-a-cyano-3-phenoxybenzyl (IR)-cis-3-(2,2-dibromovinyl)-2,2-dimethylcyclopropanecarboxylate;
(±)-a-cyano-4-fluoro-3-phenoxybenzyl (+)-4-difluoromethoxy-a-(1-methylethyl)benzeneacetate;
(RS)-a-cyano-4-fluoro-3-phenoxybenzyl;
(IRS)-cis,trans-3-(2,2-dichlorovinyl-2,2-dimethylcyclopropanecarboxylate;
S-methyl N-(methylcarbamoyloxy)thio-acetimidate;
2,3-dihydro-2,2-dimethyl-7-benzofuranyl-methylcarbamate;
2-methyl-2-(methylthio)propanol O-[(methylamino)carbonyl]oxime;
O,O-diethyl-S-(tert-butylthiomethyl)phosphorodithioate;
O,O-dimethyl S-phthalimidomethyl phosphorodithioate;
O-2,4-dichlorophenyl O-ethyl S-propyl phosphorodithioate;
O-4-bromo-2-chlorophenyl O-ethyl S-propyl phosphorothioate;
2-(dimethylamino-5,6-dimethyl-4-pyrimidinyl dimethylcarbamate;
S-6-chloro-2,3-dihydro-2-oxobenzoxazol-3-ylmethyl O,O-diethyl phosphorodithioate;
N,N-dimethyl-2-methylcarbamoyloximino-2-(methylthio)acetamide;
1-methylethyl (E,E)-11-methoxy-3,7-11-trimethyl-2,4-dodecadienoate;
S-2,3-dihydro-5-methoxy-2-oxo-1,3,4-thiadiazol-3-ylmethyl O,O-dimethyl phosphorodithioate;
O,S-dimethyl phosphoramidothioate;
2-(diethoxyphosphinylimino)-4-methyl-1,3-dithiolane;
(RS)-a-cyano-3-phenoxybenzyl N-(2-chloro-a,a,a-trifluoro-p-tolyl)-D-valinate;
4-chlorophenyl-3-(2,6-difluorobenzoylures;
O,O-diethyl O-3,5,6-trichloro-2-pyridyl phosphorothioate;
N'-(4-chloro-2-methylphenyl)-N,N-dimethylmethanimidamide;
1,3-di(carbamoylthio)-2-dimethylaminopropane;
N-methylbis(2,4-xylyliminomethyl)amine;
O,S-dimethyl acetylphosphoramidothioate.

FORMULATIONS

The cinnamamide compounds of the present invention are especially active as systemic insecticidal and acaricidal agents when made available to the root systems of plants to be protected from attack by these pests. As such, it is advantageous to apply these compounds to the soil or water in which the plants are grown. Therefore, these cinnamamides may be formulated into dry flowable compositions, granular formulations, compressed granular formulations, wettable powders, dusts, dust concentrates and microemulsions, all of which lend themselves to soil or water application and provide the requisite plant protection. Such formulations include the compounds of the invention admixed with inert, pharmacologically-acceptable solid or liquid diluents.

For example, wettable powders, dusts and dust concentrate formulations of the invention can be prepared by grinding together about 3% to 20%, by weight, of the cinnamamide compound, with about 3% to 20% by weight of a solid anionic surfactant. One suitable such anionic surfactant is a dioctyl ester of sodium sulfosuccinic acid, specifically Aersol OTB ® surfactant marketed by the American Cyanamid Company. About 60% to 94%, by weight, of an inert solid diluent, such as montmorillonite, attapulgite, chalk, talc, kaolin, diatomaceous earth, limestone, silicates or the like also is used in such formulations.

Compacted granules especially useful for soil or water application can be prepared by grinding together in about equal parts, usually about three (3) to 20 parts, of the cinnamamide and a solid surfactant, with about 60 to 94 parts of gypsum. Thereafter, the mixture is compacted into small granular particles, about 24/48 mesh or larger.

Other suitable solid surfactants useful in the present formulations include not only the anionic dioctyl ester of sodium sulfosuccinic acid but also nonionic block copolymers of ethylene oxide and propylene oxide. Such block copolymers are marketed by BASF Wyandotte Corporation as Pluronic 10R8 ®, 17R8 ®, 25R8 ®, F38 ®, F68 ®, F77 ® or F87 ®, and are especially effective for the preparation of compacted granules.

In addition to the powders and concentrate formulations described hereinabove, wettable powders and flowables may be used because they may be dispersed in water. Preferably, such flowables will be applied at the water with the aqueous compositions being sprayed on the foliage of plants to be protected. These sprays also may be applied to the breeding ground, food supply or habitat of the insects and acarina sought to be controlled.

Where solid formulations of the compounds of this invention are to be used in combination treatments with other pesticidal agents, the formulations can be applied as an admixture of the components or may be applied sequentially.

Similarly, liquid formulations of the cinnamamide in combination with other pesticidal agents may be tank mixed or may be applied separately, sequentially, as liquid sprays. Liquid spray formulations of the compounds of the invention should contain about 0.001% by weight of the active cinnamamide.

The following examples are presented as illustrations of the present invention and are not limitative thereof.

EXAMPLE 1

Preparation of p-fluorohippuric acid

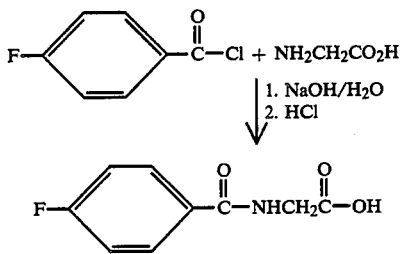

A solution of glycine (15 g, 0.2 mol) in 175 mL of 5% aqueous sodium hydroxide is cooled to 10° C. to 15° C. p-Fluorobenzoyl chloride (31.6 g, 0.2 mol) is then added, dropwise, to the mixture and stirred vigorously for 0.5 hour, while maintaining the temperature of the mixture at about 10° C. to 15° C. The pH of the reaction mixture is maintained at pH>9 by the dropwise addition at 50% aqueous sodium hydroxide. The mixture is stirred at 10° C. to 15° C. for two hours with the resulting clear solution then acidified with concentrated HCl to pH=1. The resulting product is filtered off, washed with water (2×100 mL) and air dried to give a white solid (30.8 g, 78.1%); mp=161°–163° C.

Employing the above procedure but substituting benzoyl chloride or an appropriately substituted benzoyl chloride for p-fluorobenzoyl chloride provides the hippuric acids listed in Table I.

TABLE I

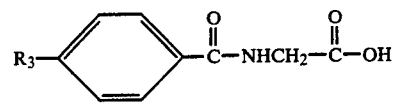

| $R_3$ | Melting Point °C. |
|---|---|
| H | 188.5–190.0 |
| Cl | 142.0–144.5 |
| C(CH₃)₃ | 182.0–185.0 |

TABLE I-continued

| $R_3$ | Melting Point °C. |
|---|---|
| CH₃O | 157.0–161.0 |
| CN | 189.0–193.0 |

EXAMPLE 2

Preparation of α-(5-oxo-2-phenyl-2-oxazolin-4-ylidene)-p-tolunitrile

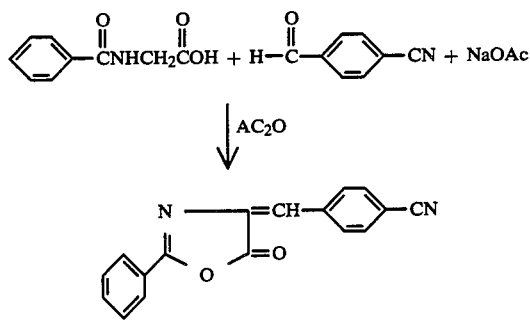

A slurry of hippuric acid (17.9 g, 0.1 mol), p-cyanobenzaldehyde (13.1 g, 0.1 mol) and anhydrous sodium acetate (8.2 g, 0.1 mol) in 150 mL of acetic anhydride is heated slowly to 90° C. on a steam bath to form a thick yellow solid. Heating is continued for two hours. The reaction mixture is then cooled to about 10° C. to 15° C., and 150 mL of water are added, dropwise, over 30 minutes. After stirring for one hour, the resulting solid is filtered off, washed with water (100 mL) and cold absolute ethanol (50 mL) and air dried to give yellow crystals (23.2 g, 85%); mp 219°–221° C.

Using the above procedure but substituting the appropriately-substituted benzaldehyde for p-cyano-benzaldehyde and the appropriately-substituted hippuric acid for hippuric acid yields the oxazolinones listed in Table II.

TABLE II

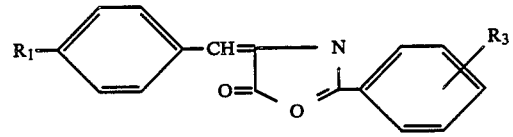

| Compound | | Melting Point °C. |
|---|---|---|
| $R_1$ | $R_3$ | |
| H | H | 165.0–165.5 |
| N(CH₃)₂ | H | 214.0–216.0 |
| CH₃O | H | 158.0–159.0 |
| NO₂ | H | 238.0–239.0 |
| CH₃ | H | 140.0–141.0 |
| Cl | H | 197.0–198.0 |
| CF₂HS | 4-CH₃O | 155.0–156.0 |
| Cl | 4-CN | >265.0 |
| Cl | 2-CH₃ | 205.0–207.0 |
| CF₃ | H | 173.0–174.0 |
| C(CH₃)₃ | H | 146.0–147.0 |
| CF₃ | 4-Cl | 196.0–197.5 |
| CF₂HCF₂O | H | 136.0–138.0 |
| CF₃O | 4-Cl | 150.0–152.5 |
| Cl | 4-C(CH₃)₃ | 161.0–163.0 |

TABLE II-continued

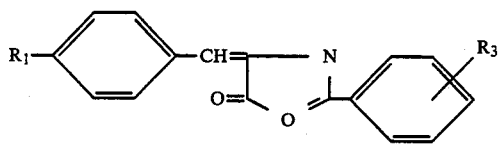

| Compound R₁ | R₃ | Melting Point °C. |
|---|---|---|
| Cl | 4-CH₃O | 213.0–215.0 |
| CF₃O | 4-CH₃O | 170.0–172.0 |
| Br | H | 205.0–207.0 |
| CH₃ | H | 135.0–138.0 |
| CF₃O | 4-F | 136.0–138.0 |
| CN | H | 219.0–221.0 |
| CN | 4-F | 217.0–218.0 |
| CH₃SO₂O | H | 173.0–174.0 |
| CF₂HS | H | 131.0–133.0 |
| Cl₂CHCF₂O | H | 131.0–132.0 |
| n-C₄H₉O | H | 125.0–127.0 |
| CH₃CONH | H | 238.0–239.5 |
| CHBr₂CF₂ | H | 139.0–140.5 |
| CF₃CH₂O | H | 159.0–160.0 |

EXAMPLE 3
Preparation of p-cyano-N-isopropylcinnamamide

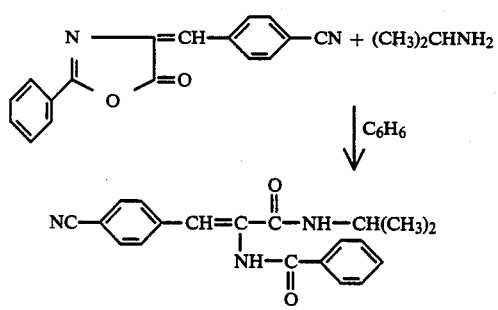

Isopropylamine (1.8 g, 0.03 mol) is added to a slurry of α-(5-oxo-2-phenyl-2-oxazolin-4-ylidene)-p-tolunitrile (5.5 g, 0.02 mol) in 100 mL of dry benzene. The temperature rises to 37° C. and the solid dissolves. After stirring the reaction mixture at room temperature for one hour and heating at reflux for three hours, the reaction mixture is then cooled to room temperature and the resulting solid is removed by filtration. Recrystallization from 2-propanol gives a pale yellow crystal product (5.5 g, 83%); mp=212°–213° C.

Following the above procedure and using the appropriately substituted oxazolinone and the appropriate amine yields the cinnamamides listed in Table III.

TABLE III

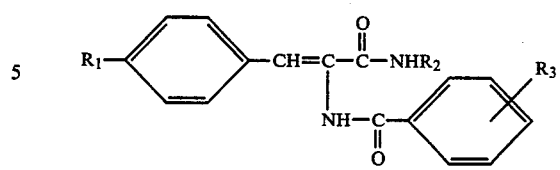

| R₁ | R₂ | R₃ | Melting Point °C. |
|---|---|---|---|
| CHF₂CF₂O | CH(CH₃)₂ | H | 183.0–185.0 |
| Cl | CH(CH₃)₂ | H | 196.0–197.0 |
| CN | CH(CH₃)₂ | H | 212.0–213.0 |
| F | CH(CH₃)₂ | H | 182.0–183.0 |
| CH₃SO₂O | CH(CH₃)₂ | H | 164.0–166.0 |
| CF₃O | Cyclopropyl | H | 194.0–196.0 |
| CF₃O | CH(CH₃)₂ | H | 209.0–211.5 |
| CF₂HO | CH(CH₃)₂ | H | 194.0–195.0 |
| F | Cyclopropyl | H | 187.0–188.0 |
| CF₂HO | CH(CH₃)(C₂H₅) | H | 195.5–196.0 |
| CF₂HO | Cyclopropyl | H | 181.0–181.5 |
| CH₃CH₂SO₂O | CH(CH₃)₂ | H | 163.0–165.0 |
| CH₃—CO—NH | CH(CH₃)₂ | H | 200.0–200.5 |
| CH₃—SO₂—O | CH(CH₃)(C₂H₅) | H | 169.5–170.5 |
| CH₃—SO₂—O | C(CH₃)₃ | H | 209.0–210.0 |
| C₂H₅ | CH(CH₃)₂ | H | 201.0–203.0 |
| CHCl₂CF₂O | CH(CH₃)₂ | H | 173.0–174.0 |
| C₂H₅O | CH(CH₃)₂ | H | 193.0–194.0 |
| CN | C(CH₃)₃ | H | 204.0–205.0 |
| CF₂HS | CH(CH₃)₂ | H | 200.0–202.0 |
| CHBr₂CF₂ | CH(CH₃)₂ | H | 172.0–174.0 |
| CF₃CH₂O | CH(CH₃)₂ | H | 159.0–160.0 |
| CHF₂CF₂O | CH(CH₃)(C₂H₅) | H | 176.0–178.0 |
| Cl | CH(CH₃)₂ | H | 186.0–188.0 |
| Cl | CH(CH₃)₂ | 4-CN | 186.5–189.0 |
| Cl | CH(CH₃)₂ | 3-CH₃ | 227.0–228.0 |
| Br | CH(CH₃)₂ | H | 199.0–200.0 |
| Cl | C(CH₃)₃ | H | 222.0–223.0 |
| NO₂ | CH(CH₃)₂ | H | 210.0–211.0 |
| Cl | CH(CH₃)₂ | 4-C(CH₃)₃ | 175.0–177.0 |
| H | CH(CH₃)₂ | H | 164.0–166.0 |
| Cl | CH(CH₃)₂ | 4-OCH₃ | 173.5–175.0 |
| Cl | CH(CH₃)(C₂H₅) | H | 194.0–195.0 |
| CF₃O | CH(CH₃)₂ | 4-Cl | 187.0–188.5 |
| CHF₂CF₂O | Cyclopropyl | H | 186.0–188.0 |
| CF₃O | CH(C₂H₅)₂ | H | 210.0–212.0 |
| Cl | Cyclopropyl | H | 206.0–207.0 |
| CF₃ | CH(CH₃)₂ | H | 203.0–204.0 |
| CH₃SO₂O | Cyclopropyl | H | 157.0–159.0 |

What is claimed is:

1. A compound having the formula:

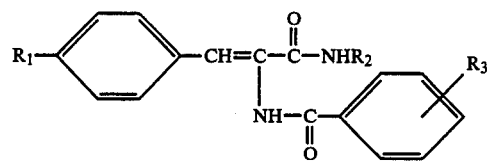

wherein R₁ is hydrogen, C₁–C₄ alkyl, C₁–C₄ alkoxy, CF₃CH₂O, CF₃O, F, Cl, Br, CF₃, NO₂, CF₂HS, CF₂HO, (R)₂N, R-SO₃, R-CO-NH or CHY₂CF₂O; Y is F, Cl or Br; R is C₁–C₄ alkyl; R₂ is CH₃, C₂H₅, branched C₃–C₅ alkyl or cyclopropyl; R₃ is hydrogen, Cl, C₁–C₄ alkyl, C₁–C₄ alkoxy or CN.

2. A compound according to claim 1, wherein R₁ is CF₃CH₂O, CF₃O, F, Cl, Br, CF₃, NO₂, CF₂HS, CF₂HO, R-SO₃, R-CO-NH or CHY₂CF₂O; R₃ is hydrogen; Y is F, Cl or Br; R is C₁–C₄ alkyl; and R₂ is CH₃, C₂–C₅ alkyl or cyclopropyl.

3. A compound according to claim 1, α-benzamide-N-isopropyl-p-(1,1,2,2-tetrafluoroethoxy)-cinnamamide.

4. A compound according to claim 1, α-benzamido-p-chloro-N-isopropylcinnamamide.

5. A compound according to claim 1, α-benzamido-p-fluoro-N-isopropylcinnamamide.

6. A compound according to claim 1, α-benzamido-p-hydroxy-N-isopropylcinnamamide methanesulfonate (ester).

7. A compound according to claim 1, α-benzamido-N-cyclopropyl-p-(trifluoromethoxy)cinnamamide.

8. A compound according to claim 1, α-benzamido-N-isopropyl-p-(trifluoromethoxy)cinnamamide.

9. A compound according to claim 1, α-benzamido-p-(difluoromethoxy)-N-isopropylcinnamamide.

10. A compound according to claim 1, α-benzamido-N-cyclopropyl-p-fluorocinnamamide.

11. A compound according to claim 1, α-benzamido-N-cyclopropylcinnamamide.

12. A compound according to claim 1, α-benzamido-N-sec-butyl-p-(difluoromethoxy)cinnamamide.

13. A compound according to claim 1, α-benzamido-p-hydroxy-N-isopropylcinnamamide ethanesulfonate (ester).

* * * * *